US012661229B2

(12) United States Patent (10) Patent No.: US 12,661,229 B2
Bapat et al. (45) Date of Patent: Jun. 23, 2026

(54) SYSTEMS AND METHODS FOR HEART VALVE REPAIR

(71) Applicant: THE TRUSTEES OF COLUMBIA UNIVERSITY IN THE CITY OF NEW YORK, New York, NY (US)

(72) Inventors: Vinayak Nilkanth Bapat, New York, NY (US); Shalaka Vinayak Bapat, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1172 days.

(21) Appl. No.: 17/370,917

(22) Filed: Jul. 8, 2021

(65) Prior Publication Data

US 2021/0330461 A1 Oct. 28, 2021

Related U.S. Application Data

(63) Continuation of application No. PCT/US2020/012808, filed on Jan. 8, 2020.

(60) Provisional application No. 62/934,606, filed on Nov. 13, 2019, provisional application No. 62/789,612, filed on Jan. 8, 2019.

(51) Int. Cl.
*A61F 2/24* (2006.01)

(52) U.S. Cl.
CPC .......... *A61F 2/2454* (2013.01); *A61F 2/2457* (2013.01); *A61F 2/2466* (2013.01); *A61F 2220/0016* (2013.01); *A61F 2220/0091* (2013.01)

(58) Field of Classification Search
CPC .... A61F 2/2454; A61F 2/2457; A61F 2/2466; A61F 2220/0016; A61F 2220/0091
See application file for complete search history.

(56) References Cited

U.S. PATENT DOCUMENTS

| | | | |
|---|---|---|---|
| 7,569,062 B1 | 8/2009 | Kuehn et al. | |
| 7,635,329 B2 | 12/2009 | Goldfarb et al. | |
| 10,517,726 B2 * | 12/2019 | Chau ..................... | A61F 2/2454 |
| 10,631,982 B2 * | 4/2020 | Hammer ............... | A61F 2/2427 |
| 2004/0049211 A1 * | 3/2004 | Tremulis ............... | A61F 2/2487 |
| | | | 623/1.36 |
| 2006/0178700 A1 | 8/2006 | Quinn | |
| 2007/0197858 A1 | 8/2007 | Goldfarb et al. | |
| 2010/0174363 A1 * | 7/2010 | Castro ................... | A61F 2/2436 |
| | | | 623/2.11 |
| 2012/0277853 A1 * | 11/2012 | Rothstein .............. | A61F 2/2457 |
| | | | 623/2.11 |
| 2014/0257475 A1 * | 9/2014 | Gross ..................... | A61F 2/246 |
| | | | 623/2.38 |

(Continued)

FOREIGN PATENT DOCUMENTS

WO 2018/017279 A1 1/2018

OTHER PUBLICATIONS

International Search Report and Written Opinion in PCT/US2020/012808, Mar. 25, 2020, 15 pages.

*Primary Examiner* — Jerrah Edwards
*Assistant Examiner* — Aren Patel
(74) *Attorney, Agent, or Firm* — BakerHostetler

(57) ABSTRACT

The disclosed subject matter relates to a system for trans-catheter heart valve repair, including a sheath; at least two clips each comprising: a ventricular jaw, an atrial jaw, and a cable; and a locking mechanism.

23 Claims, 27 Drawing Sheets

(56)  References Cited

U.S. PATENT DOCUMENTS

| | | | |
|---|---|---|---|
| 2016/0157862 A1* | 6/2016 | Hernandez | A61B 17/1227 |
| 2016/0158008 A1 | 6/2016 | Miller et al. | |
| 2016/0317290 A1 | 11/2016 | Chau et al. | |
| 2018/0185154 A1* | 7/2018 | Cao | A61F 2/2463 |
| 2019/0000623 A1 | 1/2019 | Pan et al. | |
| 2020/0085577 A1* | 3/2020 | Vola | A61F 2/2466 |
| 2021/0113332 A1* | 4/2021 | Benichou | A61F 2/2418 |

* cited by examiner

TV

S

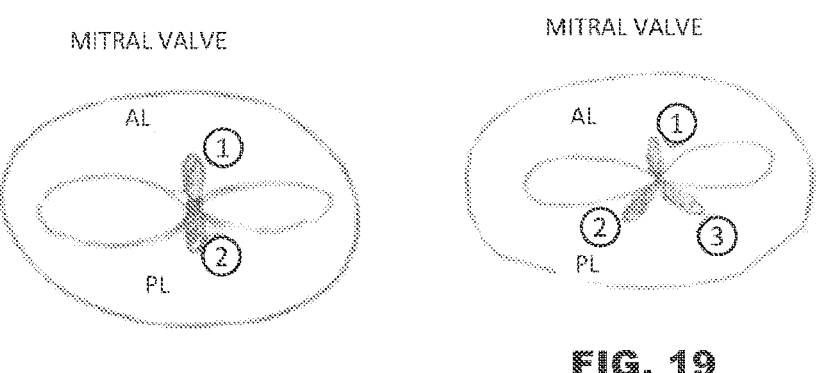
FIG. 18
FIG. 19
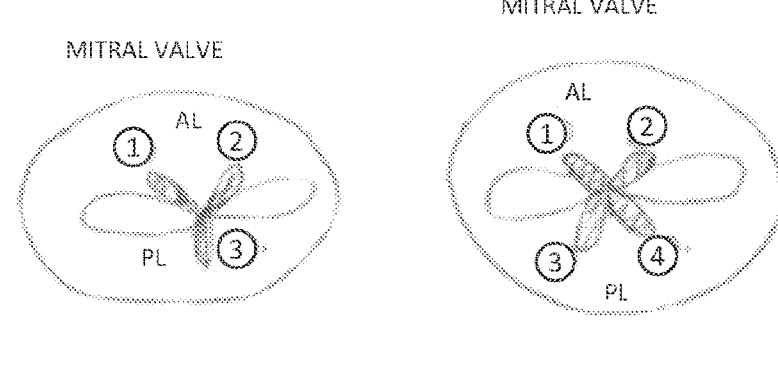
FIG. 20
FIG. 21
FIG. 22

318     ATRIAL JAW WITH
        CLEATS

321

VENTRICULAR JAW
WITH HOLLOW SPACE
316     TO ACCOMMODATE
        LEAFLET

418     ATRIAL JAW WITH
        HOLLOW SPACE

421

VENTRICULAR JAW
WITH SERRATIONS
TO CLASP THE
416     LEAFLET 518    521

ATRIAL JAW WITH
CLEATS

VENTRICULAR JAW
WITH OR
WITHOUT
SERRATIONS

516

AML          PML

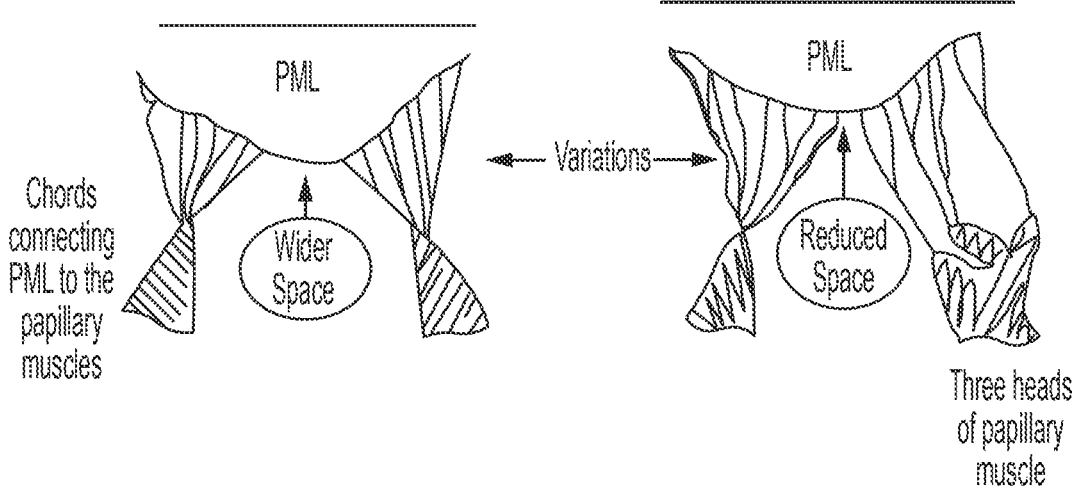
FIG. 30                              FIG. 31

FIG. 36(A)        FIG. 37(A)
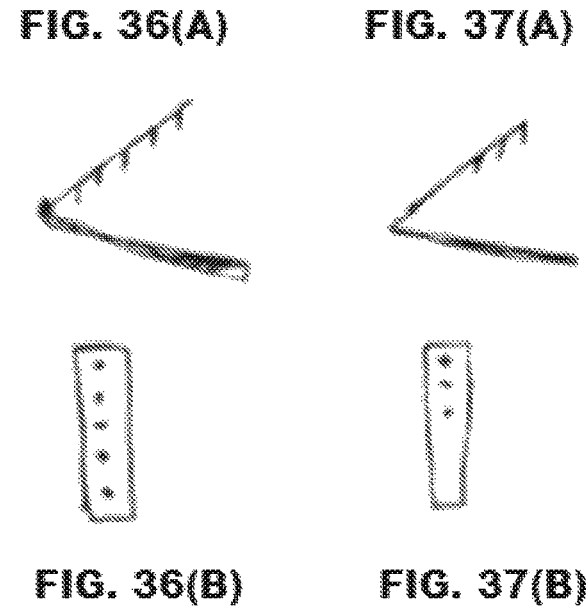
FIG. 36(B)        FIG. 37(B)
FIG. 38(A)        FIG. 39(A)
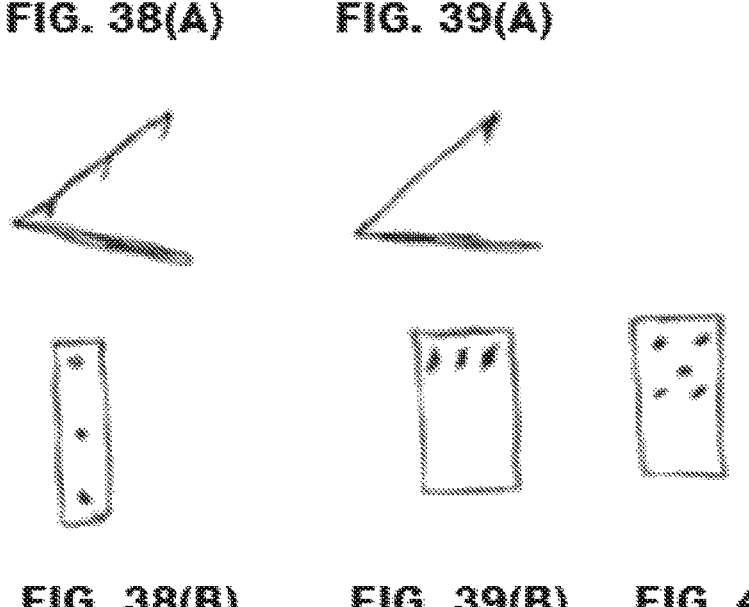
FIG. 38(B)      FIG. 39(B)      FIG. 40

ANCHOR WITH
ARTIFICIAL CHORD
IS PLACED IN LEAFLET

VCLIP CONTAINING
CATHETER IS
"RAIL-ROADED" ON
THE CHORD AND
LEAFLET IS CAPTURED
WITH THE V-CLIP

CHORD LENGTH
ADJUSTED WITH
COUPLER

CHORD CUT AND
SYSTEM WITHDRAWN

SYSTEMS AND METHODS FOR HEART VALVE REPAIR

CROSS-REFERENCE TO RELATED APPLICATIONS

This application is a continuation of PCT/US2020/012808 filed Jan. 8, 2020, which claims priority to U.S. Provisional Application 62/789,612 filed Jan. 8, 2019 and U.S. Provisional Application 62/934,606 filed Nov. 13, 2019, all of which are incorporated by reference in their entirety herein.

FIELD

The disclosed subject matter relates to apparatuses and systems for heart valve repair.

DESCRIPTION OF RELATED ART

Mitral and Tricuspid heart valves allow unidirectional passage of blood from the atrium to the ventricle and prevent regurgitation back in to the atrium during ventricular contraction. When the leaflet coaptation fails, regurgitation results. Failure of coaptation can be simply because of the dilatation of the ventricle resulting in stretching of the annulus and/or leaflet tethering, referred to as secondary regurgitation. Regurgitation can also result from abnormal leaflets, abnormal papillary muscles/chordae and is referred to as Primary regurgitation.

Mitral valve anatomy: The mitral valve MV controls the blood flow between the left atrium and the left ventricle. As illustrated in FIG. 1, mitral valve MV has two leaflets, anterior leaflet AL and posterior leaflet PL. The anterior leaflet AL is larger in area, and the posterior leaflet PL is crescentic. The coaptation line LOC is semilunar. Both leaflets are supported by fan-like chordae tendenae which attach the leaflets to the papillary muscles. (FIG. 2).

Tricuspid valve anatomy: The tricuspid valve TV, as the name suggests, is made of three leaflets (anterior leaflet AL, posterior leaflet PL and septal leaflet SL) and controls the flow between the right atrium and right ventricle. (FIG. 3). Similar to the mitral valve MV, it is also connected the papillary muscled and the ventricle by chordae tendenae.

Mitral regurgitation affects more than 10% of the general population aged 75 years and older. Previously, treatment of severe mitral regurgitation consisted exclusively of surgical mitral valve repair or replacement. In some pathologies where both treatments could be difficult or would take a longer time, Alfieri stitch has been utilized, especially in the treatment of the Mitral valve. (FIG. 4) This stitch AS approximates the two leaflets of the Mitral valve MV in the middle, thereby converting the mitral valve orifice in to a double orifice O1/O2. A similar concept of applying a stitch S has also been used in the repair of the tricuspid valve TV with some success. (FIG. 5). Because of the increased risk of surgery (mainly associated with aging and impaired left ventricular function), about 50% of patients who present with severe symptomatic mitral regurgitation and tricuspid regurgitation are unsuitable for open heart surgery. Moreover, in-hospital mortality after mitral valve surgery in octogenarians has been reported to be as high as 6% after mitral valve repair and 13% after mitral valve replacement. Mortality following tricuspid surgery is also high.

There are other approaches in the market. However, they do not allow a possibility of attaching a chordal structure between the clip and the ventricle if needed independent or in addition to the clipping mechanism.

Accordingly, less invasive procedures that are more suitable for elderly patients with associated comorbidities address an unmet clinical need.

SUMMARY

A system for transcatheter heart valve repair is provided, including a sheath; at least two clips each including: a ventricular jaw, an atrial jaw, and a cable; and a locking mechanism.

In some embodiments, the locking mechanism is configured to lock the at least two clips together or to lock the cables of each clip together.

In some embodiments, the system includes three clips.

In some embodiments, the system includes four clips.

In another aspect, a method for heart valve repair is provided, including inserting a sheath into a chamber of the heart of a patient; inserting at least two clips into said sheath using a dedicated delivery system, wherein each of said clips includes a ventricular jaw, an atrial jaw, and a cable; clipping a first leaflet of a valve in said patient's heart with a first of said at least two clips; and clipping a second leaflet of a valve in said patient's heart with a second of said at least two clips.

In some embodiments, the method further includes clipping one of the first leaflet, the second leaflet, and a third leaflet of said valve in said patient's heart with a third clip.

In some embodiments, the method further includes clipping one of the first leaflet, the second leaflet, and the third leaflet of said valve in said patient's heart with a fourth clip; and securing said at least two clips together by a locking mechanism.

In some embodiments, the locking mechanism is configured to lock together the cables holding each clip.

In some embodiments, the method further includes further includes cutting the cables of each of said at least two clips and removing said cables from said sheath.

In some embodiments, the sheath is inserted into the left atrium of said heart of said patient.

In some embodiments, the valve is a mitral valve.

In some embodiments, the valve is a tricuspid valve.

In another aspect, a system for transcatheter heart valve repair is provided, including a sheath; at least two clips each including: a ventricular jaw having a first width and a first length, an atrial jaw having a second width and second length, and a cable; and a locking mechanism.

In some embodiments, the first width and the second width are different.

In some embodiments, the first length and the second length are different.

In some embodiments, the system includes three or more clips.

In some embodiments, the locking mechanism is configured to lock the at least two clips together or to lock the cables of each clip together.

In another aspect, a system for transcatheter heart valve repair is provided, including a sheath; at least two clips each including: a ventricular jaw defining a first plurality of teeth on an interior portion thereof for engaging a leaflet of the heart valve, an atrial jaw defining a second plurality of teeth on an interior portion thereof for engaging a leaflet of the heart valve, and a cable; and a locking mechanism.

In some embodiments, the first plurality of teeth is different from the second plurality of teeth.

In another aspect, a system for transcatheter heart valve repair is provided, including a sheath, at least two clips each including: a ventricular jaw, an atrial jaw, and a cable; and a locking mechanism adapted to engage the clips in a plurality of configuration In some embodiments, the locking mechanism is configured to lock the at least two clips together or to lock the cables of each clip together.

In some embodiments, the locking mechanism includes a coupler to lock the at least two clips together, In some embodiments, the coupler allows the clips to be attached such that complete inversion of the leaflets is achieved.

In some embodiments, the coupler allows the clips to be attached such that 50% inversion of the leaflets is achieved.

In some embodiments, the coupler allows the clips to be attached such that 0-10% inversion of the leaflets is achieved.

In some embodiments, the coupler includes a hinge mechanism.

In some embodiments, the coupler defines a plurality of slots to grasp the clips in a plurality of positions.

In some embodiments, the coupler is flexible to grasp the clips in a plurality of positions In another aspect, a system for transcatheter heart valve repair is provided, including a sheath; an anchor and an artificial chord coupled to the anchor, the anchor configured for securement to a heart ventricle at least one clip slidable over the chord, the clip including a ventricular jaw, an atrial jaw, and a locking mechanism configured to secure the clip to the chord.

In another aspect, a method for heart valve repair is provided, including providing an anchor and an artificial chord coupled to the anchor; providing a clip slidable over the chord, the clip including a ventricular jaw and a ventricular jaw, inserting a sheath into a chamber of the heart of a patient; inserting the anchor and artificial chord into the chamber of the heart; securing the anchor in the ventricle on the heart; sliding the clip over the artificial chord; clipping a first leaflet of a valve in said patient's heart with said clip; and securing the position of said clip on the artificial chord with the locking mechanism.

In some embodiments, the method further includes cutting the artificial chord outside the chamber of the heart.

In some embodiments, the method further includes withdrawing the artificial chord.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 18-21 illustrate several configurations of the clip on the mitral valve in accordance with exemplary embodiments of the disclosed subject matter.

FIG. 22 illustrates a configuration of the clip on the tricuspid valve in accordance with exemplary embodiments of the disclosed subject matter.

FIGS. 26-31 illustrate the morphology of the valve configuration of a human subject.

FIG. 36(A) illustrates a side view of a clip in accordance with exemplary embodiments of the disclosed subject matter.

FIG. 36(B) illustrates an elevation view of a clip in accordance with exemplary embodiments of the disclosed subject matter.

FIG. 37(A) illustrates a side view of a clip in accordance with exemplary embodiments of the disclosed subject matter.

FIG. 37(B) illustrates an elevation view of a clip in accordance with exemplary embodiments of the disclosed subject matter.

FIG. 38(A) illustrates a side view of a clip in accordance with exemplary embodiments of the disclosed subject matter.

FIG. 38(B) illustrates an elevation view of a clip in accordance with exemplary embodiments of the disclosed subject matter.

FIG. 39(A) illustrates a side view of a clip in accordance with exemplary embodiments of the disclosed subject matter.

FIG. 39(B) illustrates an elevation view of a clip in accordance with exemplary embodiments of the disclosed subject matter.

FIG. 40 illustrates an elevation view of a clip in accordance with exemplary embodiments of the disclosed subject matter.

DETAILED DESCRIPTION OF EXEMPLARY EMBODIMENTS

Various aspects of the apparatuses and methods disclosed herein are described more fully hereinafter with reference to the accompanying drawings. This disclosure may, however, be embodied in many different forms and should not be construed as limited to any specific structure or function presented throughout this disclosure.

One of the features of mitral and tricuspid valve is variability of the leaflet in terms of length, width, quality of tissue, number and arrangement of the chords, presence of clefts and variable subvalval apparatus morphology.

The present disclosure provides devices, systems and methods that use a clip design to facilitate capture of individual valve leaflets or similar structures and, if needed, to provide a mechanism to couple with another clip of similar design.

The devices, systems and methods of the present disclosure can provide increased surgical flexibility and enable the use of multiple clips in a custom configuration for valve repair. The devices, systems and methods can mitigate the risk of stenosis and avoid the need for simultaneously clipping of valve leaflets or difficulty in clipping valve leaflets due to anatomical abnormalities and varying heart geometries. The devices, systems and methods of the present disclosure can also enable repair of the tricuspid valve and avoid issues with surgical imaging and improve steerability during surgery.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The apparatus can include a clip, delivery system and a mechanism to ensure locking of individual clips together. The clip 21, also referred to as a "V-Clip" herein, includes three elements, a ventricular jaw 16, an atrial jaw 18 and a cable 20. (FIG. 11) The design of each portion may vary according to the need as will described in greater detail herein.

Figure 1:
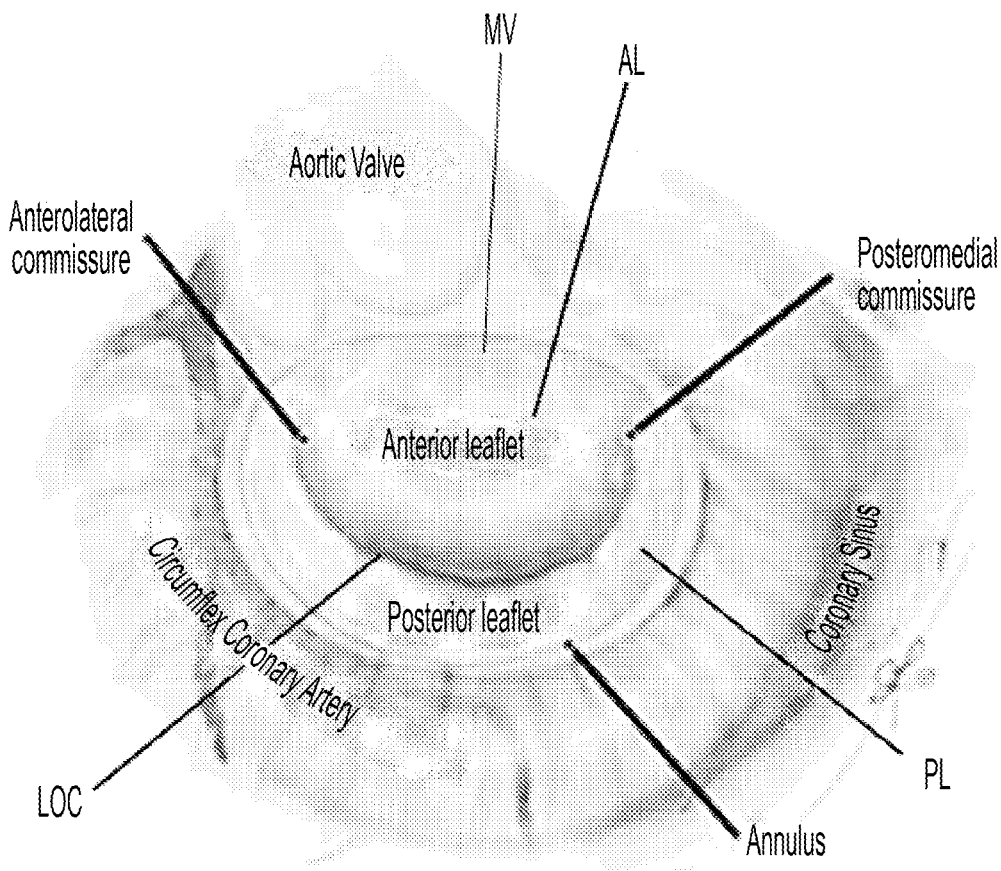
FIGS. 1 and 2 illustrate the structure of the mitral valve of the human heart.
Figure 2:
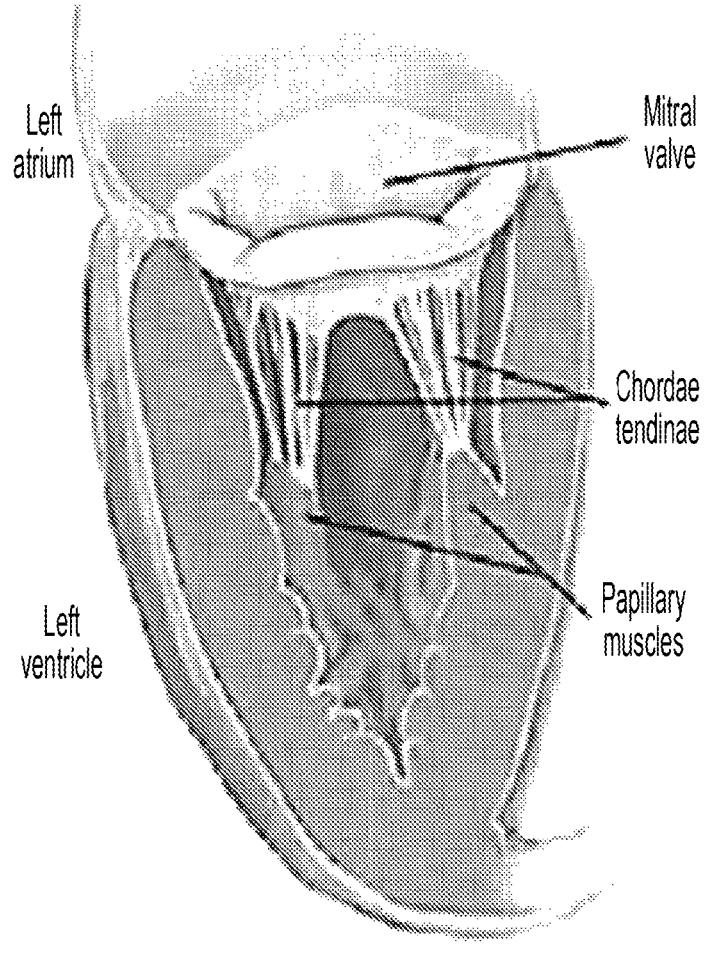
Figure 3:
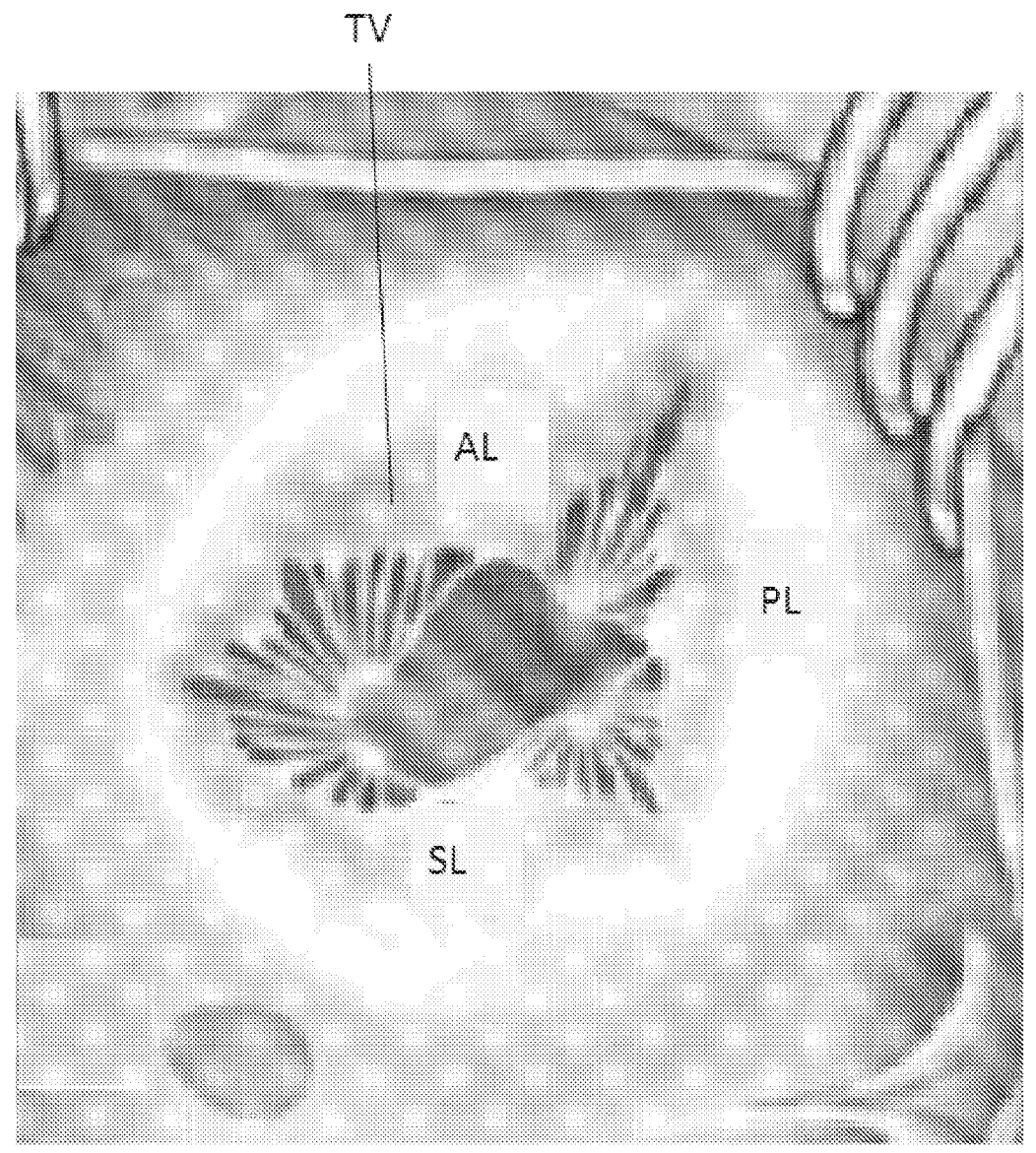
FIG. 3 illustrates the structure of the tricuspid valve of the human heart.
Figure 4:
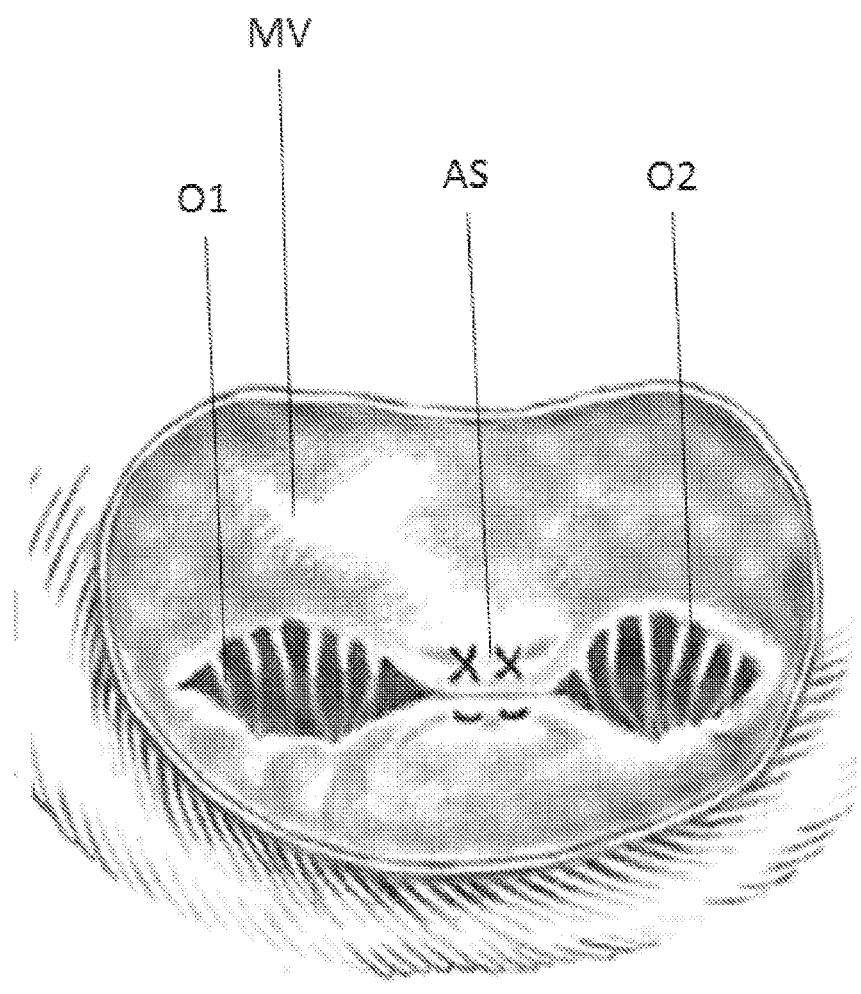
FIG. 4 illustrates a technique for repair of the mitral valve.
Figure 5:
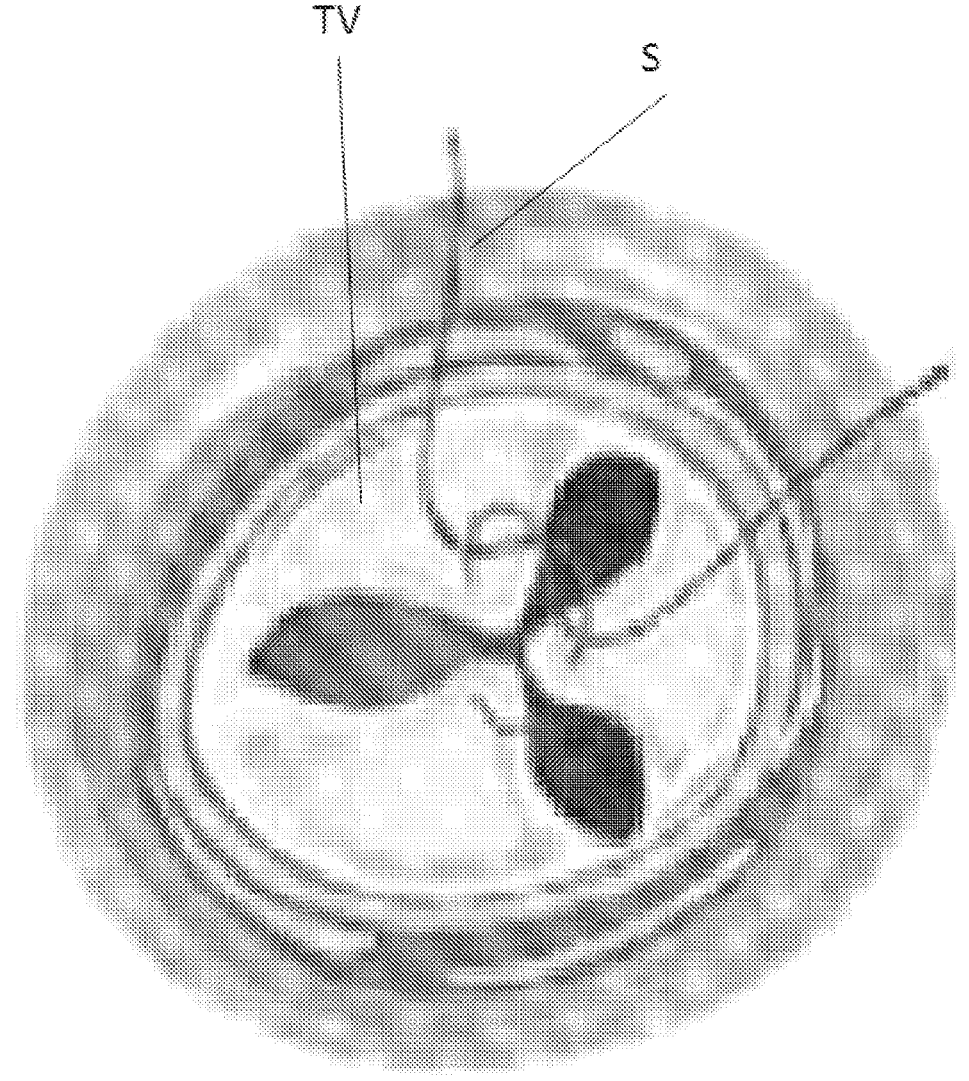
FIG. 5 illustrates a technique for repair of the tricuspid valve.
Figure 6:
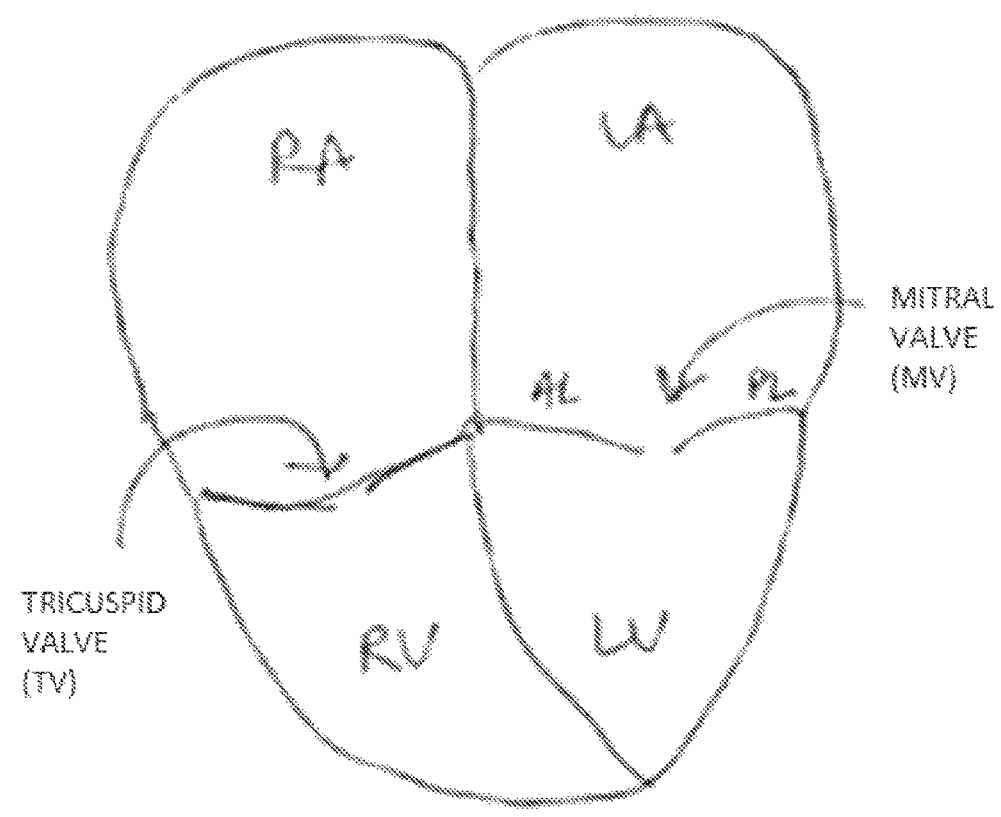
FIG. 6 illustrates a schematic cross-sectional view of the human heart.
Figure 7:
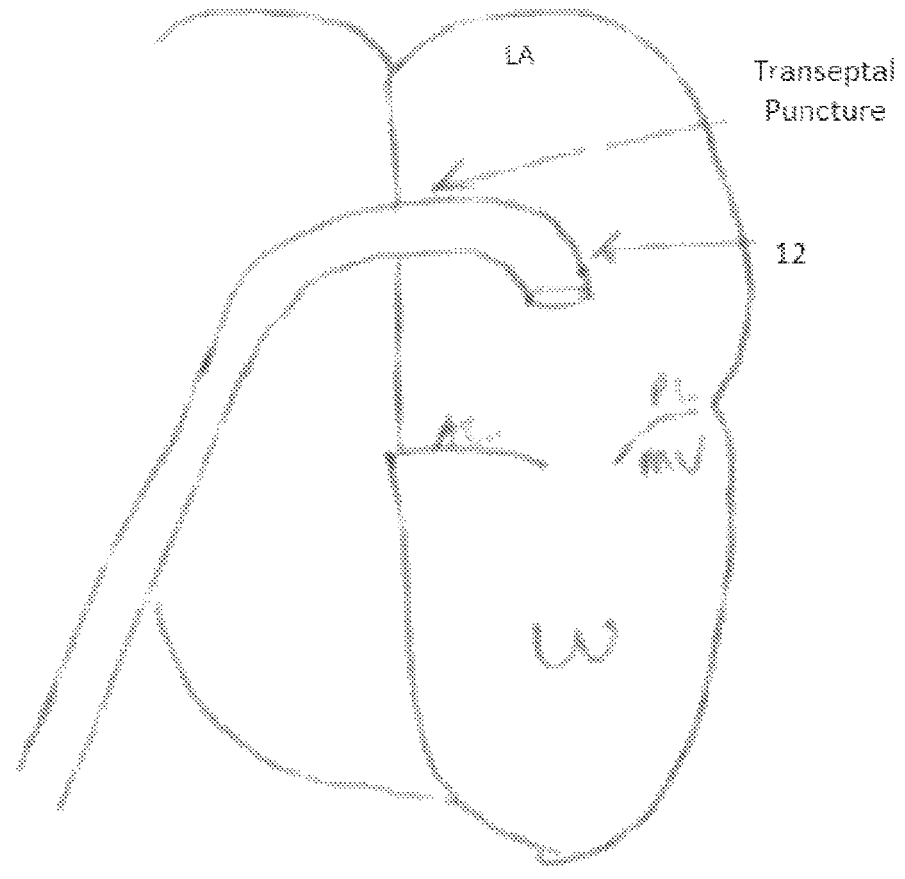
FIG. 7 illustrates an early stage in the installation of the clips in accordance with an exemplary embodiment of the disclosed subject matter.

The structure of the human heart is shown in FIG. 6, including the right atrium RA, left atrium LA, right ventricle RV, left ventricle LV, mitral valve MV, and tricuspid valve TV. As shown in FIG. 7, a sheath 12 (dedicated or commercially available) is inserted through femoral vein, through a trans-septal puncture and then in to the left atrium LA as is currently performed for a variety of procedures. In some embodiments, the sheath 12 is a steerable sheath.

Figure 8:
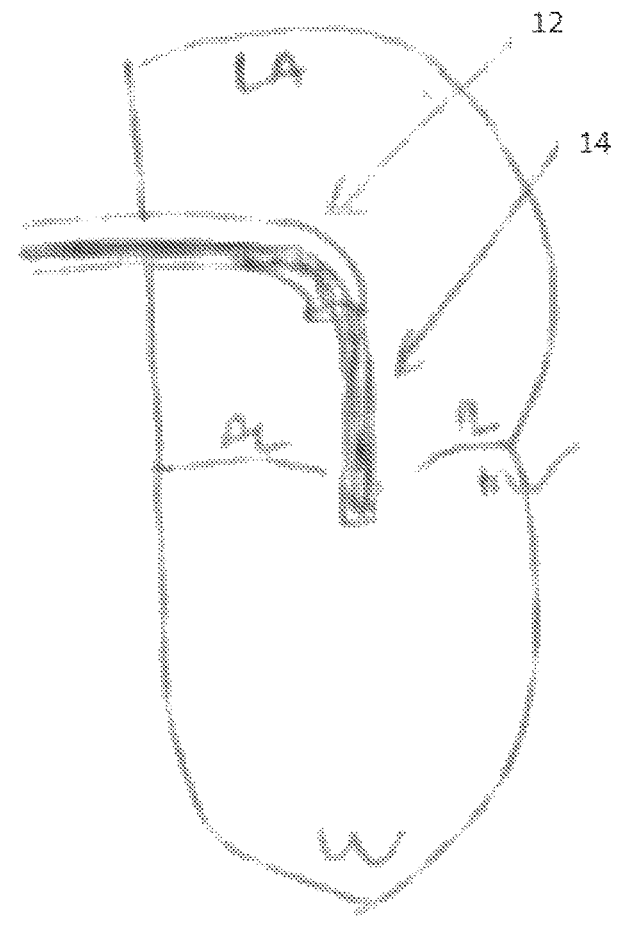
FIG. 8 illustrates a subsequent stage in the installation of the clips in accordance with an exemplary embodiment of the disclosed subject matter.

As illustrated in FIG. 8, the first V-Clip is then inserted into the left atrium through sheath 12 using a dedicated delivery system 14. The delivery system 14 may include a number of configurations. For example, the clip may be resilient or shape-memory alloy. While retained in the delivery system 14, e.g., a sleeve configuration, the clip is in a compressed or folded configuration either by the steerable sheath or an additional interior sheath.

Figure 9:
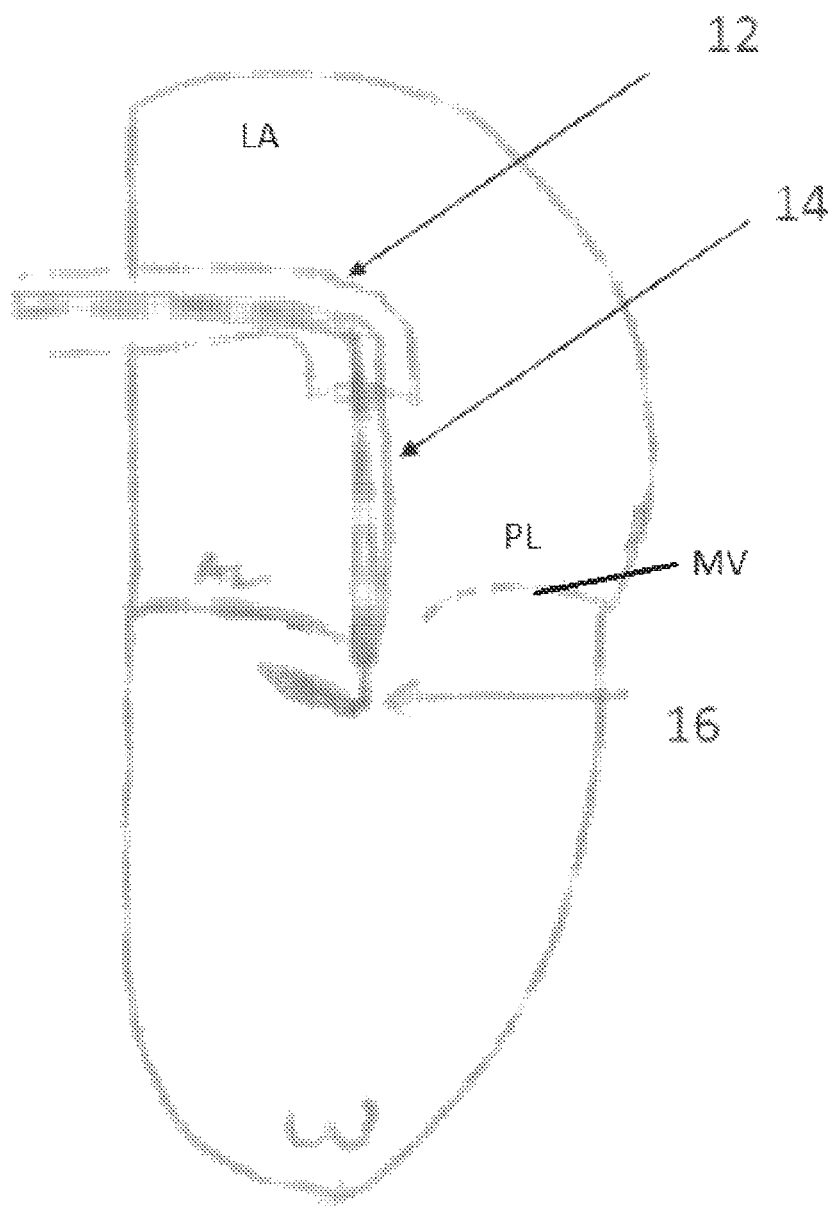
FIG. 9 illustrates a further stage in the installation of the clips in accordance with an exemplary embodiment of the disclosed subject matter.

In FIG. 9, the ventricular jaw 16 is deployed from the delivery system 14 and sheath 12, and allowed to assume an expanded configuration as shown, and positioned under one leaflet, e.g., the anterior leaflet AL.

Figures 10, 11:
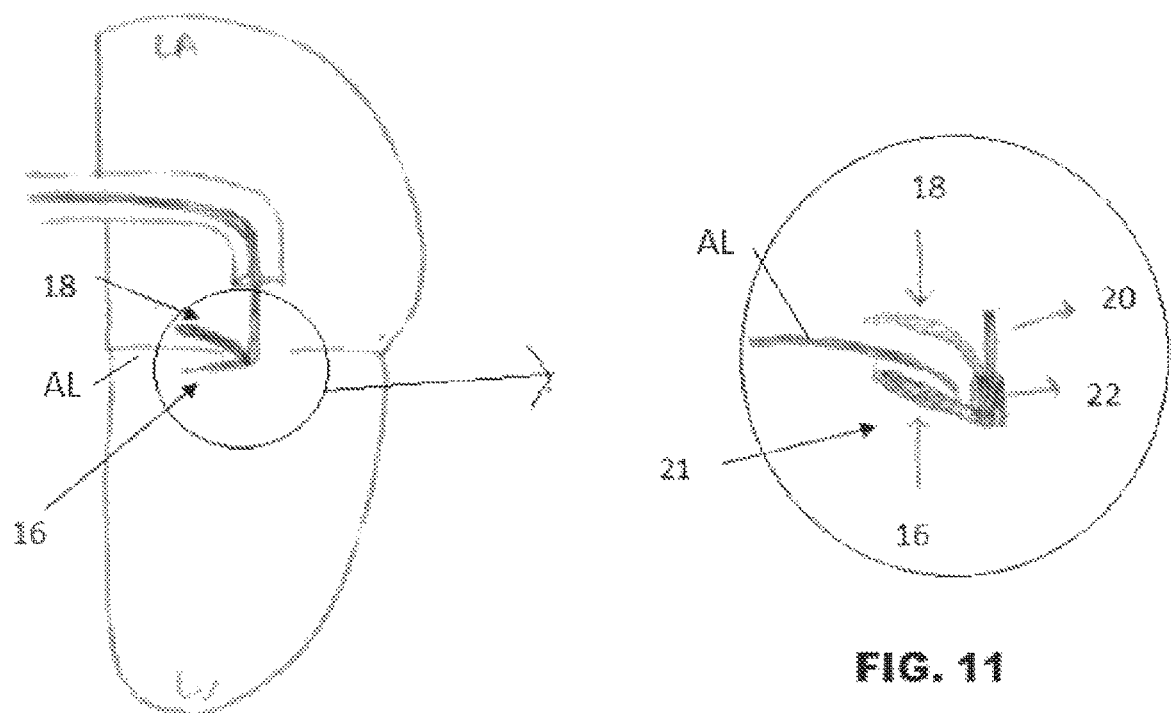
FIG. 10 illustrates an early stage in the installation of the clips in accordance with an exemplary embodiment of the disclosed subject matter.
FIG. 11 illustrates a close-up view of the clip illustrated in FIG. 10.

As shown in FIGS. 10-11, the atrial jaw 18 is deployed from the delivery system 14 and sheath 12, and allowed to assume an expanded configuration as shown. In some embodiments, both jaws 16 and 18 are exposed together and then the ventricular jaw 16 is placed under the posterior leaflet PL. The leaflet, e.g., anterior leaflet AL, is captured or "clipped" by the ventricular jaw 16 and the atrial jaw 18. For example, the clip is closed by approximating the ventricular jaw 16 and atrial jaw 18 together, and the leaflet capture is confirmed. In some embodiments, the ventricular jaw 16 and atrial jaw 18 are approximated by the use of wires, cables or the like.

Figures 12, 13:
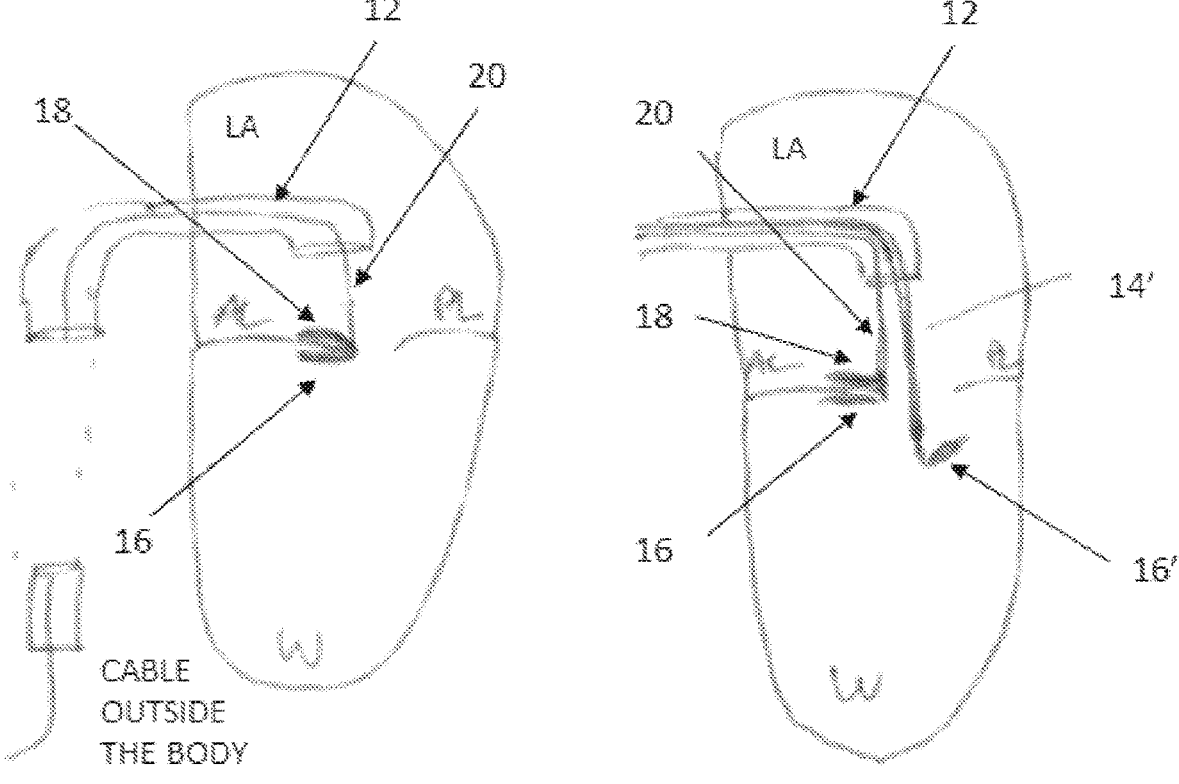
FIG. 12 illustrates a still further stage, following the stage of FIG. 10, in the installation of the clips in accordance with an exemplary embodiment of the disclosed subject matter.
FIG. 13 illustrates insertion of a second clip in accordance with an exemplary embodiment of the disclosed subject matter.

As shown in FIG. 12, the delivery system 14 is removed through the sheath 12, and the cable 20 attached to the first V-Clip is secured outside the sheath.

As illustrated in FIG. 13, a second V-Clip is introduced by a second delivery system 14'. In analogous manner as described above regarding the first clip, the ventricular jaw portion 16' can be introduced first, followed by the atrial jaw portion 18', and then the ventricular jaw 16 and atrial jaw 18 are approximated. In some embodiments, the order of the jaw portions 16/18 can be changed, or the jaw portions 16/18 can be both introduced together.

Figure 14:
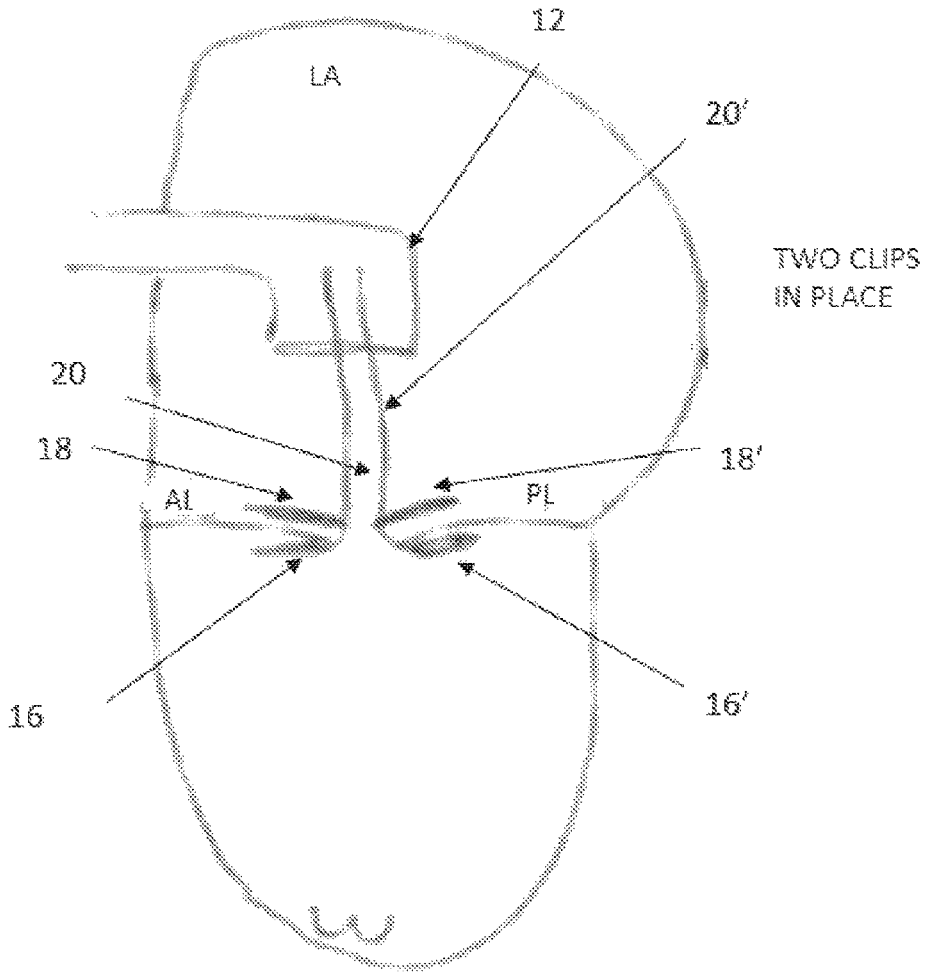
FIG. 14 illustrates the securement of the clips to valve leaflets in accordance with an exemplary embodiment of the disclosed subject matter.

This second V-clip is placed onto the other leaflet in an area identified to achieve maximum reduction of the regurgitation. (FIG. 14) It may be possible that, for example, reduction in the regurgitation could be best reduced by applying one clip on one leaflet and two on the other. In this scenario, each clip is placed on to the desired location. As each individual leaflet is captured individually, the procedure is able to accommodate differing valve physiologies with higher chance of success. For example, two, there, or four clips can be placed in this manner, with cables holding each clip being secured outside the body.

Figure 15:
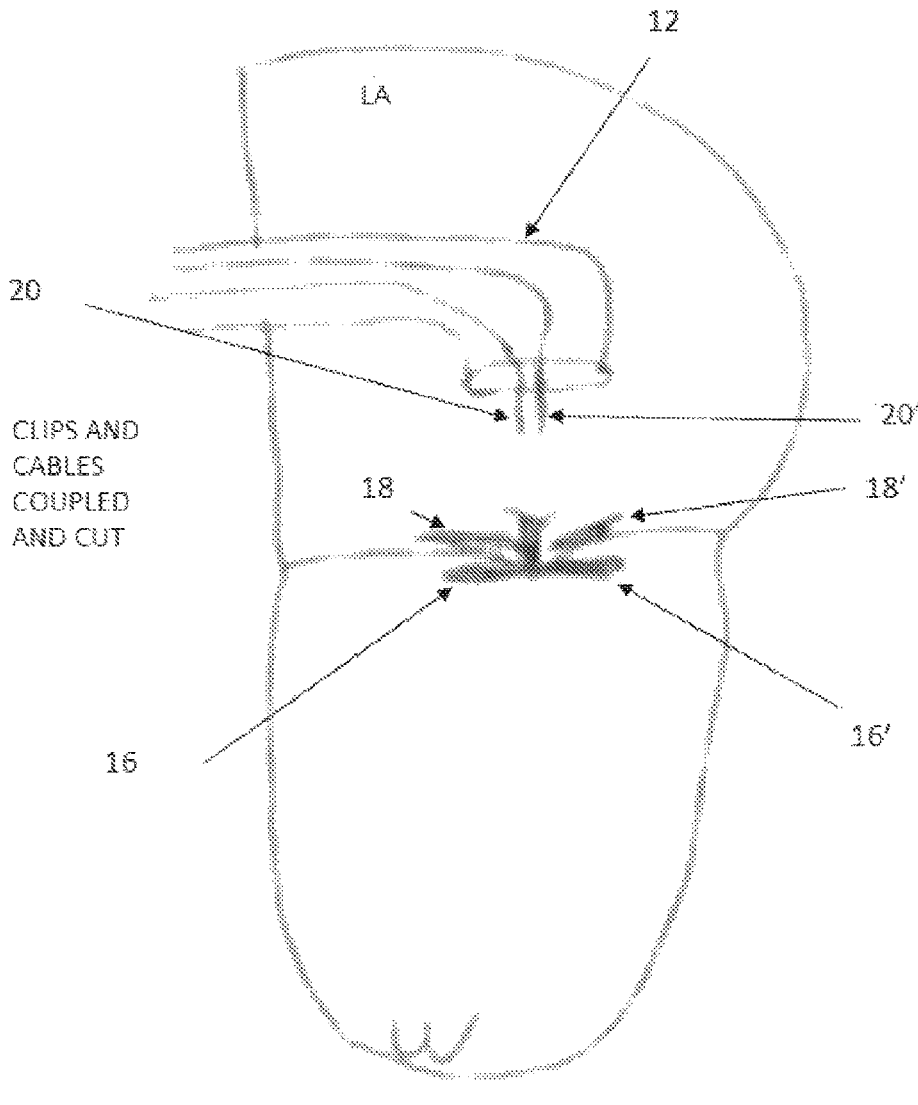
FIGS. 15-17 illustrates several techniques for clipping and coupling the clips in accordance with exemplary embodiments of the disclosed subject matter.
Figure 16:
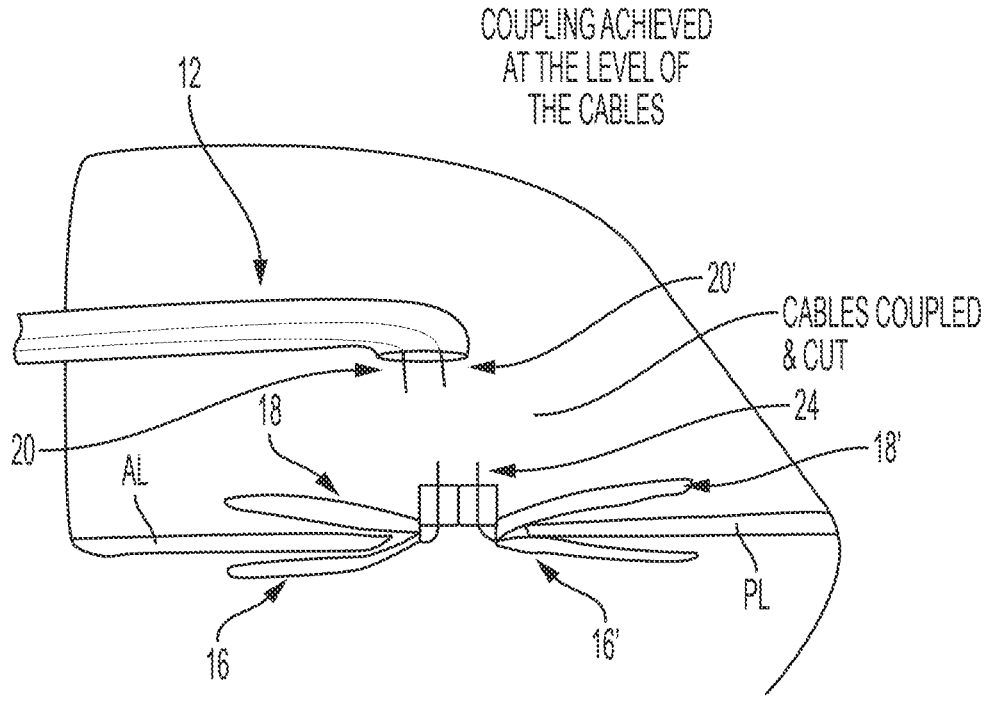
Figure 17:
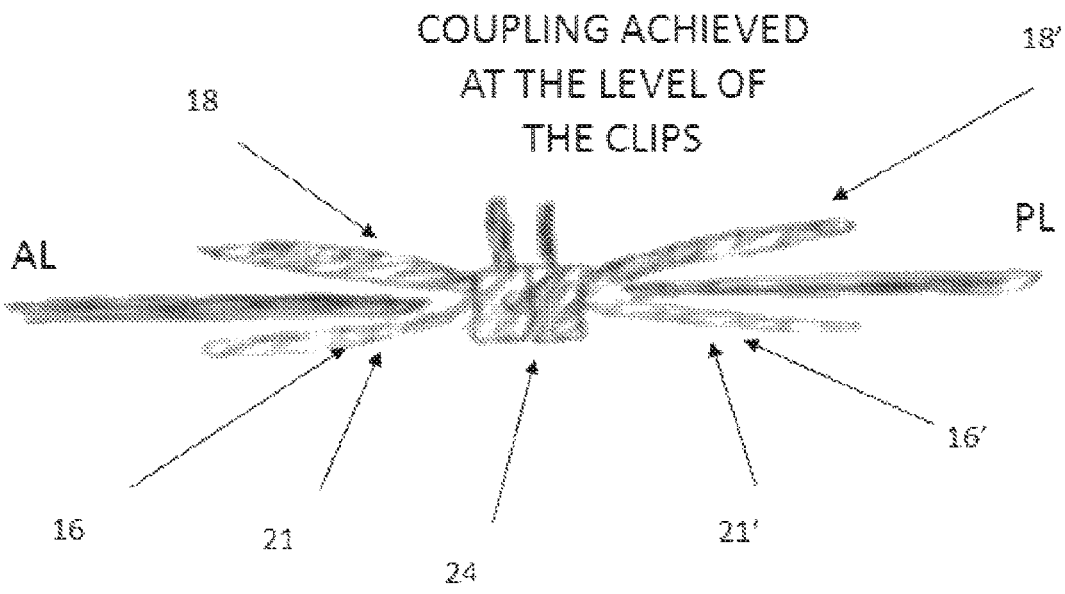

Once the jaw portions of the clips are positioned in their desired locations, the jaw portions 16/18 or 16'/18' are then coupled together, e.g., secured about the valve leaflet for long-term installation. For example, a locking mechanism 24 within the structure of the clip can be used to couple the jaws. In some embodiments, the jaws are coupled by locking the cables 20/20' holding the clip. (See FIGS. 15-17) FIG. 15 illustrates that the clip and cables are coupled together, and the cables have been cut. FIG. 16 illustrates that coupling is achieved at the level of the cables 20/20'. FIG. 17 illustrates that coupling is achieved at the level of the clips 21/21'. In some embodiments, the locking mechanism 24 is reversible to ensure satisfactory result. Such configuration would allow the position or number of the clips to be altered if necessary and if desired that one or more clips be moved or removed. Once the clips are locked together with either of the two mechanisms, the cables 20/20' are released or cut and withdrawn from the sheath.

Various placement configurations of the clips are shown in FIGS. 18-22. For example, FIGS. 18-21 illustrate the placement of the V-clip on the mitral valve relative to the anterior leaflet AL and the posterior leaflet PL. FIG. 18 illustrates two V-clips coupled together. FIGS. 19-20 illustrate alternative placements of three V-clips coupled together on the mitral valve, e.g., two clips on the ventricular leaflet (FIG. 19), or two clips on the anterior leaflet (FIG. 20). FIG. 21 illustrates four V-clips coupled together, e.g., two clips on the ventricular leaflet and two clips on the anterior leaflet. FIG. 22 illustrates three V-clips deployed on the tricuspid valve. This configuration is important to facilitate installation in the tricuspid valve having three delicate leaflets, which are usually wide apart. One of each clip is placed on the anterior leaflet AL, the posterior leaflet PL and the septal leaflet SL.

Figure 23:
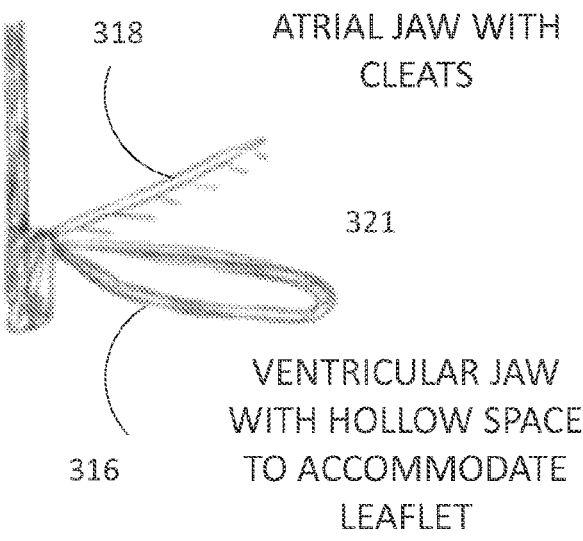
FIGS. 23-25 illustrate several configurations of the clip in accordance with exemplary embodiments of the disclosed subject matter.
Figure 24:
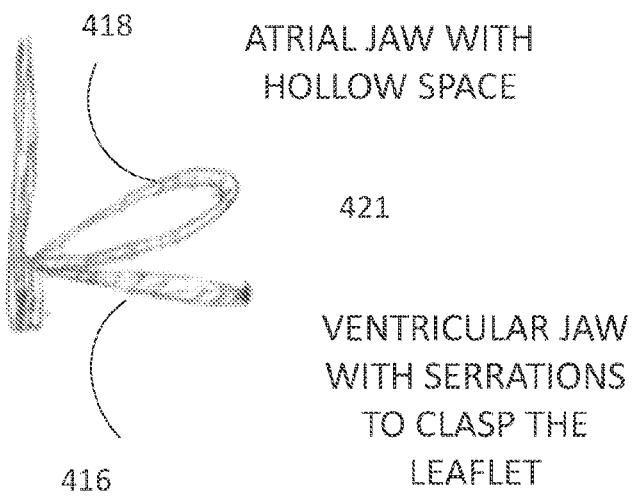
Figure 25:
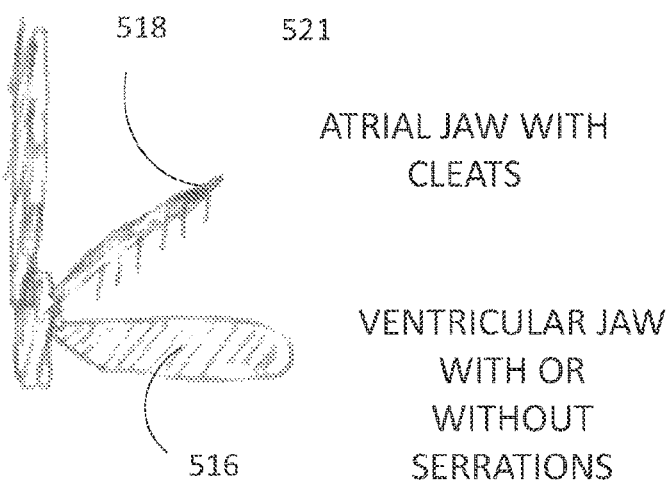

Several embodiments of the V-clip are illustrated in FIGS. 23-25. In some embodiments, the atrial and ventricular jaws have interlocking hollow jaws. In some embodiments, the atrial jaw is a clasp and the ventricular jaw is a hollow jaw. In some embodiments, the structure of the jaw is such that the jaw is compressed in to a linear shape when sheathed and expands in to a wider paddle like shape when unsheathed. In some embodiments, either of the jaws are covered with cloth or pericardial material. In some embodiments, either of the jaw vary in number of cleats/teeth to secure leaflet capture and encourage tissue growth. Opening and closing of each jaw may be controlled separately, thus allowing secure placement clip.

In FIG. 23, the V-clip 321 includes a ventricular jaw 316 with a hollow space to accommodate the leaflet and an anterior jaw 318 with cleats. In FIG. 24, the V-clip 421 includes an anterior jaw 418 with a hollow space to accommodate the leaflet and a ventricular jaw 416 with serrations to clasp the leaflet. In FIG. 25, the V-clip 521 includes an anterior jaw 518 with cleats and a ventricular jaw 516 with serrations, or alternatively without serrations.

Figure 26:
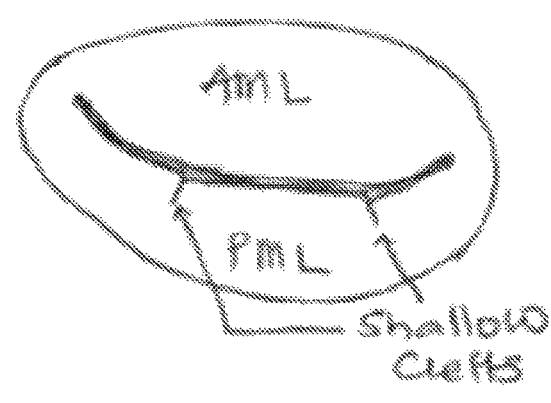
Figure 27:
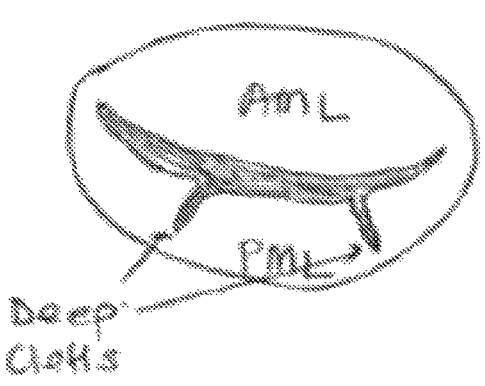
Figure 28:
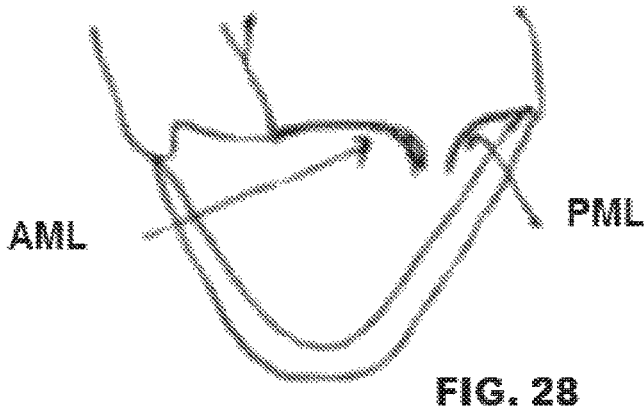
Figure 29:
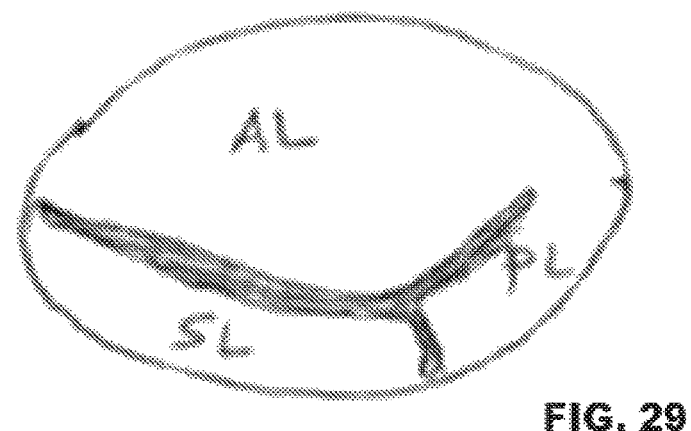

Various embodiments of the V-clip designs described herein address the variations in patient morphology. For example, the posterior mitral leaflet can have multiple clefts resulting in regurgitation (FIGS. 26-27) In some patients, the anterior mitral leaflet AML, is longer than the posterior mitral leaflet PML, and also it is tethered in many cases (FIG. 28) The septal leaflet SL of the tricuspid valve is more delicate and also attached to the right ventricle directly with chords Leaflet length and quality varies between each leaflet, thus anterior leaflet AL of both mitral and tricuspid are longer, better in quality of tissue than other leaflets, e.g., septal leaflet SL and posterior leaflet PL (FIG. 29) Among different patients, subvalval apparatus varies; the number of papillary muscles varies; and the number and assignment of chords varies. (FIGS. 30-31) Thus, similar design of clip to catch/fix all leaflet variation is probably the cause of failure and less effectiveness Embodiments of the V-clip allows for individual leaflet capture and also allow removal. The final coupling of the individual clips is achieved, and the type of clip used to effectively and securely capture each leaflet can vary.

Figure 32:
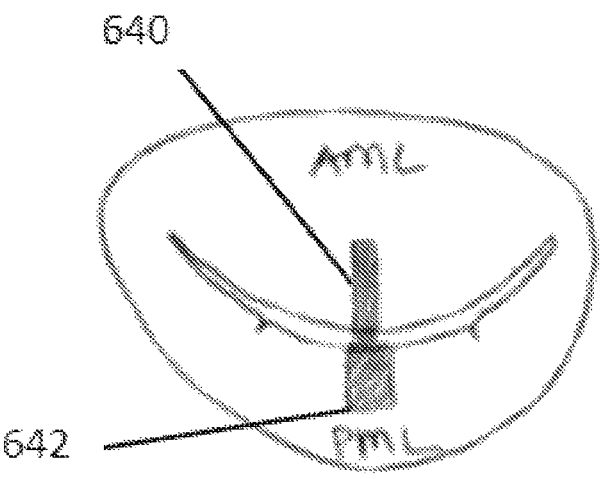
FIGS. 32-35 illustrate several configurations of the clip in accordance with exemplary embodiments of the disclosed subject matter.
Figure 33:
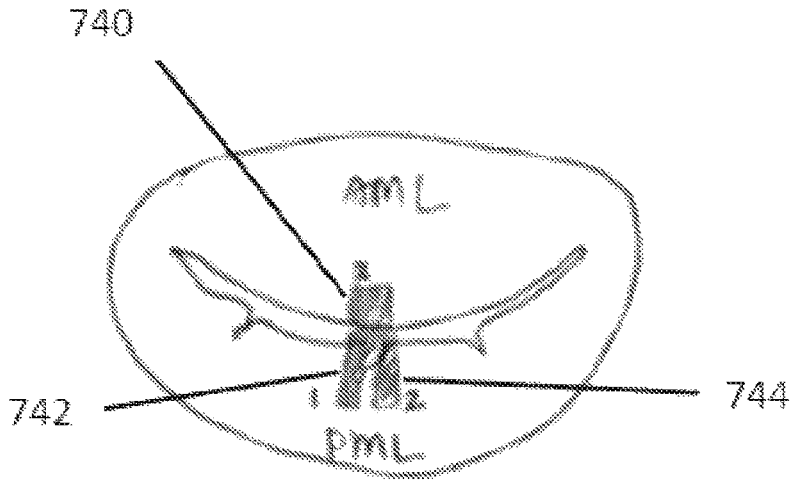
Figure 34:
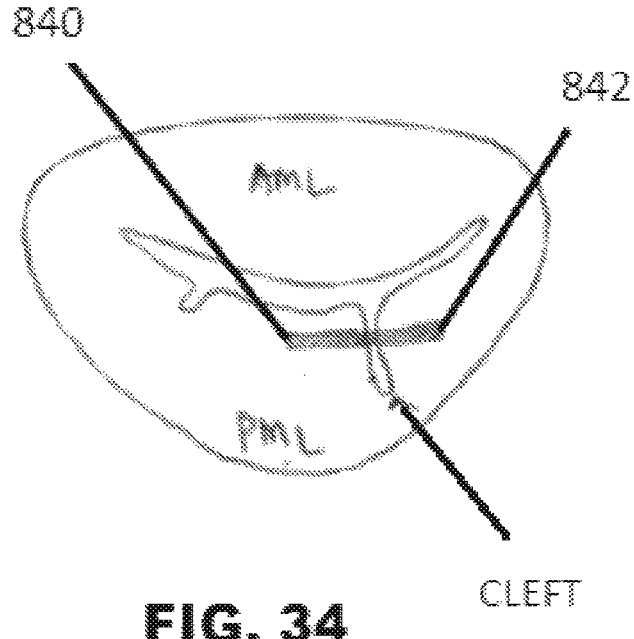
Figure 35:
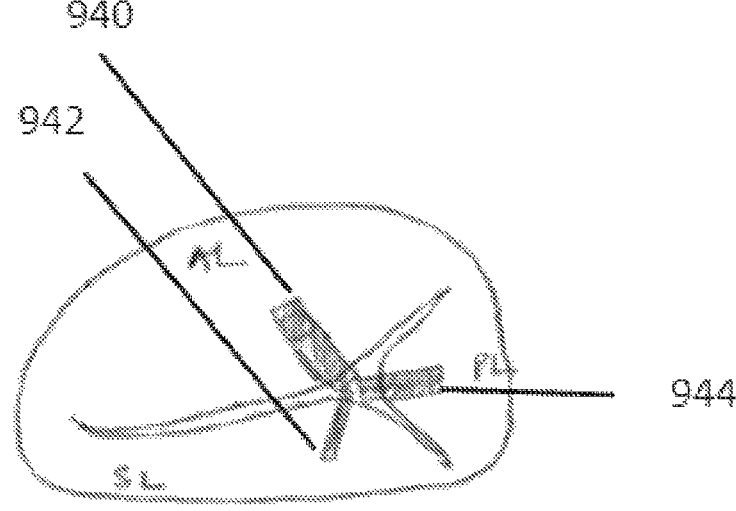

As illustrated in FIG. 32, a clip 640 used to capture posterior mitral leaflet can be wider and shorter in a given situation, coupled with anterior clip 642 which is longer and thinner. As illustrated in FIG. 33, two thinner and longer clips 742, 744 used on either side of the clefts straddling a chord can be coupled with a single clip 740 anteriorly. As illustrated in FIG. 34, two clips 840, 842 can be used horizontally to close a cleft. As illustrated in FIG. 35, three clips 940, 942, 944 of different length and width can be used to couple tricuspid leaflets together.

As illustrated in FIGS. 36(A)-40, grasping mechanism are provided to cooperate with the type of leaflet used in each surgical situation. For example, when the anterior leaflet is thicker and bulky, a clip with more rows of teeth can be used, whereas grasping the posterior leaflet having a clip with fewer teeth can be used to avoid damage to the leaflet. FIG. 36(A) is a side view and FIG. 36(B) is an elevation view of a clip having 5 teeth on the anterior jaw. FIG. 37(A) is a side view and FIG. 37(B) is an elevation view of a clip having three teeth on the distal end of the anterior jaw. FIG. 38(A) is a side view and FIG. 38(B) is an elevation view of a clip having three teeth equally spaced along the length of the anterior jaw. FIG. 39(A) is a side view and FIG. 39(B) is an elevation view of a clip having three teeth equally spaced laterally on the anterior jaw. FIG. 40 is an elevation view of a clip having five teeth distributed on the distal end of the anterior jaw.

Figures 41, 42, 43:
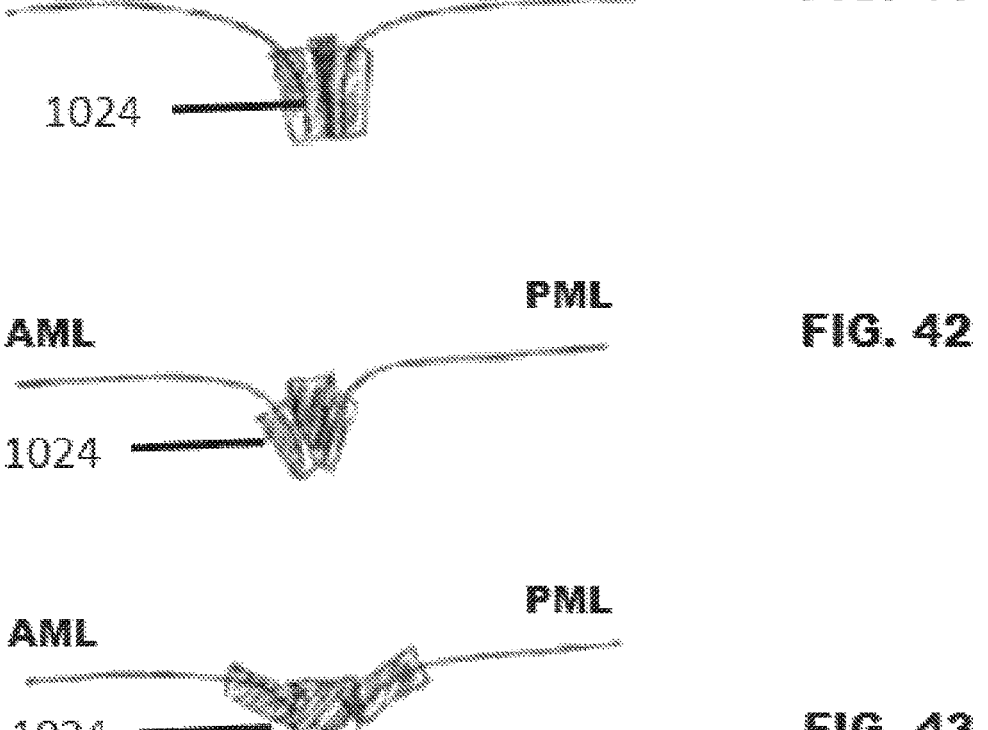
FIGS. 41-43 illustrate several position of a coupling mechanism in accordance with exemplary embodiments of the disclosed subject matter.

In some embodiments, the coupling mechanism 1024 is used to bring together the leaflets to different degree of closeness and eversion/inversion (FIGS. 41-43)

When fully coupled, the leaflet edge is inverted and opposed but when partially coupled they may still be close to bridge the clip but only partly inverted.

In case the leaflets are too far apart, the "coupler 1024 can be designed in such a way so as to fill the gap. This versatility will increase the ability to bridge varying degrees of leaflet gap without the need of lengthening the length of the clip and will reduce the excessive tension of the leaflets which occurs with existing devices when the gap is too wide, resulting in leaflet tears, clip detachment and/or residual MR. For example, the coupler may include hinges, elongated slots, or may be flexible in order to accommodate different positions of the leaflets.

Figure 44:
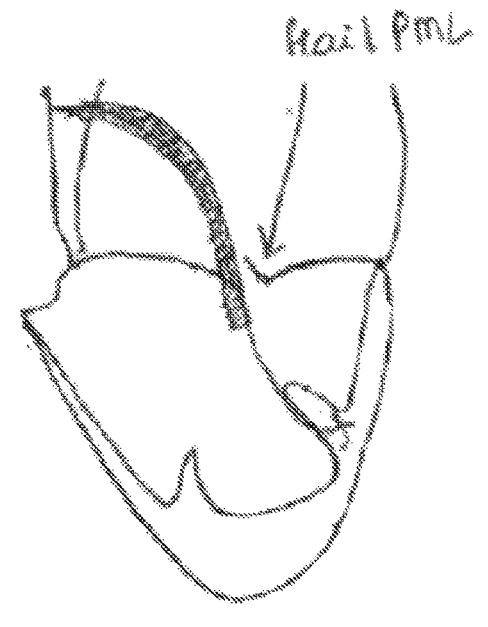
FIGS. 44-47 illustrate the stages of the installation of a chord and clip in the human heart in accordance with exemplary embodiments of the disclosed subject matter.
Figure 45:
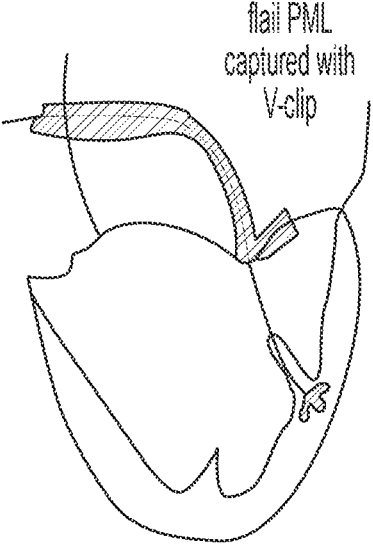

In some embodiments, the V-clip is used to implant an artificial chord to a prolapsing leaflet PML. As illustrated in FIG. 44, an artificial chord/chords of premeasured or adjustable length can be implanted on a papillary muscle or ventricle. As illustrated in FIG. 45, the V-clip is "rail roaded" on the chord mechanism or slid over the chord mechanism and then the prolapsing leaflet is grasped. The clip is released.

Figure 46:
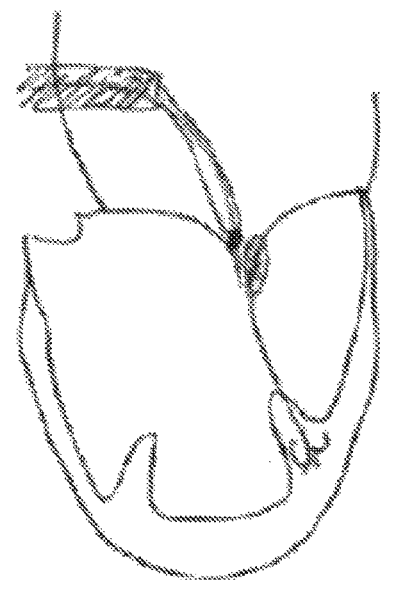
Figure 47:
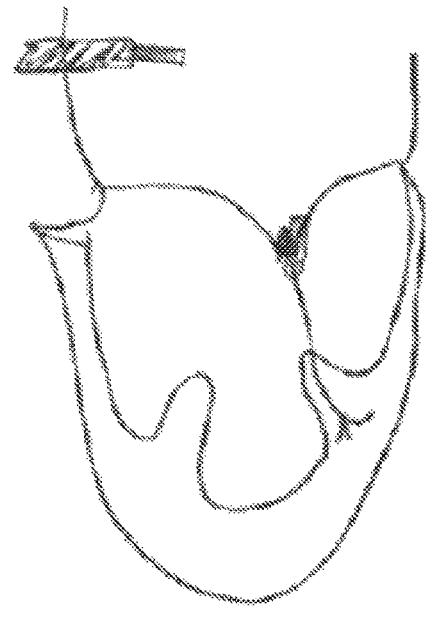

As illustrated in FIG. 46, the chord length is adjusted by using the coupler made of either metal/fabric/chordal material. The length achieved eliminates regurgitation or has desired effect. As illustrated in FIG. 47, the chord is then secured with the coupler and cut. The V-clip mechanism allows this procedure to be performed with a single catheter.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments and/or implementations can be understood and effected by those skilled in the art in practicing the claimed disclosure, from a study of the drawings, the disclosure and the appended claims.

What is claimed is:

1. A system for transcatheter heart valve repair, comprising:
   a sheath defining a lumen;
   at least two clip assemblies comprising:
   a first elongate member slidably disposed within the lumen of the sheath;
   a first clip releasably coupled to, and selectively detachable from, the first elongate member, wherein the first clip comprises a ventricular jaw and an atrial jaw, wherein the ventricular jaw and the atrial jaw of the first clip are each individually deployable to a respective position for approximation of the first clip on a first leaflet portion of the heart valve;
   a second elongate member slidably disposed within the lumen of the sheath and unconnected to the first elongate member such that the first and second elongate members are extendable out from the lumen toward the heart valve separately from each other;

a second clip that is separate from and unconnected to the first clip, wherein the second clip is releasably coupled to, and selectively detachable from, the second elongate member, wherein the second clip comprises a ventricular jaw and an atrial jaw, wherein the ventricular jaw and the atrial jaw of the second clip are each individually deployable to a respective position for approximation of the second clip on a second leaflet portion of the heart valve; and a locking mechanism configured to slide along the first elongate member and the second elongate member and to couple and lock together the first and second clips.

2. The system of claim 1, wherein the at least two clip assemblies comprises three of the clip assemblies.

3. The system of claim 1, wherein the at least two clip assemblies comprises four of the clip assemblies.

4. The system of claim 1, wherein each ventricular jaw has a first width and a first length, and each atrial jaw has a second width and second length, wherein the first width and the second width are different.

5. The system of claim 1, wherein each ventricular jaw has a first width and a first length, and each atrial jaw has a second width and second length, wherein the first length and the second length are different.

6. The system of claim 1, wherein each ventricular jaw comprises a first plurality of teeth on an interior portion thereof for engaging the first leaflet portion of the heart valve and each atrial jaw comprises a second plurality of teeth on an interior portion thereof for engaging the second leaflet portion of the heart valve.

7. The system of claim 6, wherein the first plurality of teeth is different from the second plurality of teeth.

8. The system of claim 1, wherein the locking mechanism is configured to couple and lock together the first and second clips of the at least two clip assemblies in situ, and not until the first clip is approximated on the first leaflet portion and the second clip is approximated on the second leaflet portion.

9. The system of claim 8, wherein the locking mechanism comprises a coupler to lock the first and second clips together.

10. The system of claim 9, wherein the coupler allows the first and second clips to be attached such that complete inversion of the leaflets is achieved.

11. The system of claim 9, wherein the coupler allows the first and second clips to be attached such that 50% inversion of the leaflets is achieved.

12. The system of claim 9, wherein the coupler allows the first and second clips to be attached such that 0-10% inversion of the leaflets is achieved.

13. The system of claim 9, wherein the coupler comprises a hinge mechanism.

14. The system of claim 9, wherein the coupler defines a plurality of slots to grasp the first and second clips in a plurality of positions.

15. The system of claim 9, wherein the coupler is flexible to grasp the first and second clips in a plurality of positions.

16. A method for heart valve repair, comprising:

inserting a sheath into a chamber of a heart of a patient, wherein the sheath defines a lumen;

providing at least two clip assemblies comprising:

a first elongate member slidably disposed within the lumen of the sheath;

a first clip releasably coupled to, and selectively detachable from, the first elongate member, wherein the first clip comprises a ventricular jaw and an atrial jaw, wherein the ventricular jaw and the atrial jaw of the first clip are each individually deployable to a respective position for approximation of the first clip on a first leaflet portion of the heart valve;

a second elongate member slidably disposed within the lumen of the sheath and unconnected to the first elongate member such that the first and second elongate members are extendable out from the lumen toward the heart valve separately from each other;

a second clip that is separate from and unconnected to the first clip, wherein the second clip is releasably coupled to, and selectively detachable from, the second elongate member, wherein the second clip comprises a ventricular jaw and an atrial jaw, wherein the ventricular jaw and the atrial jaw of the second clip are each individually deployable to a respective position for approximation of the second clip on a second leaflet portion of the heart valve; and individually extending the first elongate member and the first clip of the at least two clip assemblies from an end of the sheath toward the heart valve;

clipping the first leaflet portion of the heart valve with the first clip of the at least two clip assemblies by individually deploying the ventricular jaw and the atrial jaw of the first clip such that the first leaflet portion is approximated between the ventricular jaw and the atrial jaw of the first clip;

individually extending the second elongate member and the second clip of the at least two clip assemblies from an end of the sheath toward the heart valve; and clipping the second leaflet portion of the heart valve with the second clip of the at least two clip assemblies by individually deploying the ventricular jaw and the atrial jaw of the second clip such that the second leaflet portion is approximated between the ventricular jaw and the atrial jaw of the second clip.

17. The method of claim 16, further comprising clipping a third leaflet portion of the heart valve with a third clip of the at least two clip assemblies.

18. The method of claim 17, further comprising securing the first clip, the second clip, and the third clip together by advancing a locking mechanism along the elongate member of each clip assembly and into engagement with each of the first clip, the second clip, and the third clip.

19. The method of claim 16, further comprising:

providing a locking mechanism;

after the clipping of the first and second leaflet portions, advancing the locking mechanism along the first elongate member and the second elongate member; and locking the first clip and the second clip together by engaging the locking mechanism onto the first clip and the second clip.

20. The method of claim 19, further comprising, after locking the first clip and the second clip together, individually uncoupling the first elongate member from the first clip and the second elongate member from the second clip.

21. The method of claim 16, wherein the chamber is a left atrium.

22. The method of claim 16, wherein the heart valve is a mitral valve.

23. The method of claim 16, wherein the heart valve is a tricuspid valve.

* * * * *